US010219886B2

(12) United States Patent
LePage, Jr. et al.

(10) Patent No.: US 10,219,886 B2
(45) Date of Patent: Mar. 5, 2019

(54) ROLLED FLEXIBLE IMPLANTS AND DEVICE FOR DEPLOYMENT THEREOF

(71) Applicant: Atrium Medical Corporation, Hudson, NH (US)

(72) Inventors: Albert A. LePage, Jr., Nashua, NH (US); Scott E. Corbeil, Litchfield, NH (US); Anthony R. Horton, Manchester, NH (US)

(73) Assignee: Atrium Medical Corporation, Merrimack, NH (US)

( * ) Notice: Subject to any disclaimer, the term of this patent is extended or adjusted under 35 U.S.C. 154(b) by 1335 days.

(21) Appl. No.: 13/833,184

(22) Filed: Mar. 15, 2013

(65) Prior Publication Data

US 2013/0331868 A1 Dec. 12, 2013

Related U.S. Application Data

(60) Provisional application No. 61/658,696, filed on Jun. 12, 2012.

(51) Int. Cl.
*A61B 17/08* (2006.01)
*A61F 2/00* (2006.01)

(52) U.S. Cl.
CPC .......... *A61F 2/0063* (2013.01); *A61F 2/0077* (2013.01); *A61F 2002/0072* (2013.01); *F04C 2270/0421* (2013.01)

(58) Field of Classification Search
CPC ........... A61F 2/00; A61F 2/0063; A61B 17/08
See application file for complete search history.

(56) References Cited

U.S. PATENT DOCUMENTS 3,328,259 A 6/1967 Anderson
5,147,387 A 9/1992 Jansen et al.
(Continued)

FOREIGN PATENT DOCUMENTS

EP 0581036 A1 2/1994
EP 2433588 A2 3/2012
(Continued)

OTHER PUBLICATIONS

Supplemental European Search Report dated Jan. 7, 2016 issued for corresponding EP patent application No. 13803858.3, 5 pages.
(Continued)

*Primary Examiner* — Victor Nguyen
(74) *Attorney, Agent, or Firm* — Wesley Scott Ashton; Kevin T. Godlewski

(57) ABSTRACT

A deployment device for a flexible implant includes a housing and one or two chambers formed therein. When two chambers are included, the housing can have two elongate openings formed in its outer sides, each providing side access to one of the chambers, and the flexible implant can be rolled into a double-rolled configuration and placed in the chambers of the deployment device in such a way that a middle portion of the flexible implant is external to the housing. When the flexible implant is rolled and loaded in the deployment device, the flexible implant can extend out through open end(s) of the chamber(s) or can be encapsulated within the chamber(s). The flexible implant can be provided separate from the deployment device. The flexible implant can include a flexible base sheet including a body portion and a tab. A flexible separable layer can be removably disposed on the body portion.

16 Claims, 9 Drawing Sheets

(56) References Cited

U.S. PATENT DOCUMENTS

| | | |
|---|---|---|
| 5,263,969 A | 11/1993 | Phillips et al. |
| 5,304,187 A | 4/1994 | Green et al. |
| 5,464,403 A | 11/1995 | Kieturakis et al. |
| 5,480,436 A | 1/1996 | Bakker et al. |
| 5,503,623 A | 4/1996 | Tilton, Jr. et al. |
| 5,634,931 A | 6/1997 | Kugel |
| 5,957,939 A | 9/1999 | Heaven et al. |
| 6,099,518 A | 8/2000 | Adams et al. |
| 6,548,081 B2 | 4/2003 | Sadozai et al. |
| 7,947,054 B2 | 5/2011 | Eldar et al. |
| 8,920,483 B2 | 12/2014 | Swanick et al. |
| 2004/0019360 A1* | 1/2004 | Farnsworth ........... A61F 2/0063 606/151 |
| 2007/0112361 A1 | 5/2007 | Schonholz |
| 2007/0196451 A1 | 8/2007 | Singhal et al. |
| 2008/0195121 A1 | 8/2008 | Eldar et al. |
| 2009/0125041 A1 | 5/2009 | Dudai |

FOREIGN PATENT DOCUMENTS

| | | |
|---|---|---|
| WO | WO 2004/080348 A1 | 9/2004 |
| WO | 2007/056297 A2 | 5/2007 |
| WO | WO 2011/128903 | 10/2011 |

OTHER PUBLICATIONS

International Search Report for International Application No. PCT/US2013/044508, dated Sep. 6, 2013.
International Search Report for International Application No. PCT/US2013/044309, dated Sep. 4, 2013.
International Preliminary Report on Patentability issued in counterpart International Application No. PCT/US2013/044508, dated Dec. 24, 2014.
International Preliminary Report on Patentability issued in International Application No. PCT/US2013/044309, dated Dec. 24, 2014.
Examination Report issued in counterpart AU Application No. 2013274666, dated Jan. 25, 2017.
Examination Report issued in counterpart AU Application No. 2017261564, dated May 15, 2018.
Office Action issued in U.S. Appl. No. 13/839,929, dated May 7, 2014.
Non-Final Office Action issued in U.S. Appl. No. 15/817,018, dated Sep. 19, 2018.

\* cited by examiner

ROLLED FLEXIBLE IMPLANTS AND DEVICE FOR DEPLOYMENT THEREOF

RELATED APPLICATION

This application claims priority to, and the benefit of, U.S. Provisional Application No. 61/658,696, filed Jun. 12, 2012, for all subject matter common to both applications. The disclosure of said provisional application is hereby incorporated by reference in its entirety.

FIELD OF THE INVENTION

The present invention relates to single-rolled or double-rolled implants, and deployment devices suitable for use therewith. More particularly, the present invention provides a rolled implant and optionally a deployment device with one or more interior chambers adapted to releasably receive the implant in the rolled (e.g., single-rolled or double-rolled) configuration.

BACKGROUND OF THE INVENTION

In open and laparoscopic hernia repair, mesh prostheses are utilized to provide reinforcement and support at the hernia defect. Such mesh prostheses or other sheet-like prostheses (e.g., films, surgical fabrics, and the like) are inserted through a small incision cut into the skin and abdominal wall. Generally, such mesh prostheses are flat sheets (e.g., of woven or knitted surgical fabric) that are trimmed to fit the anatomy of the defect site as needed prior to being rolled up and inserted through the incision. Once inserted, the mesh prosthesis is unfolded and affixed to the defect site using sutures or tacks.

However, manipulating sheet-like prostheses during laparoscopic procedures presents numerous challenges to a surgeon. For example, trocars, when used, only provide a limited range of motion and require the user to utilize small instruments and graspers to manipulate, unroll, and position the mesh or prosthesis. Moreover, in many instances, the mechanical and physical properties of the sheet-like prostheses change once exposed to bodily conditions and environments (e.g., bodily temperatures, body fluids, etc.). In particular, when exposed to moisture, such sheet-like prostheses can hydrate and become less stiff, making them more prone to rupture or tearing during handling. Furthermore, some of the materials may have a layer of self-adhering material designed to adhere to moist tissue surfaces, which can further complicate a user's ability to handle and place the prosthesis during surgery and implantation.

Furthermore, in abdominal and pelvic laparoscopic procedures in particular, the insertion, placement, and application of such prostheses prove extremely challenging to surgeons. In particular, the aforementioned concerns are magnified by the fact that extremely thin prostheses (e.g., films) are used. As such, rupture or tear during handling is a large risk in such procedures as currently performed by doctors.

SUMMARY

Accordingly, there is a need in the art for flexible implants suitable for being deployed with greater ease of handling. Furthermore, there is a need in the art for a deployment device that enables the convenient delivery, deployment, and placement of flexible implants (e.g., meshes, films, patches, fabrics, etc.) during surgical procedures such as hernia repair. The present invention is directed toward solutions to address these and other needs, in addition to having other desirable characteristics that will be appreciated by one of skill in the art upon reading the present specification.

In accordance with example embodiment of the present invention, a deployment system is provided for a mesh or a film. The deployment system includes an elongate housing with a chamber formed therein. The chamber can have at least one open end providing access thereto. A flexible implant includes a flexible sheet base and a flexible separable layer can be removably disposed on the flexible sheet base. The implant itself can be removably disposed in the chamber of the housing in a rolled configuration about a central axis. A longitudinal dimension of the implant in the rolled configuration along its central axis can be greater than a longitudinal dimension of the chamber that is generally parallel to the central axis of the implant. A portion of the flexible sheet base can extend out through the at least one open end of the chamber.

In accordance with aspects of the present invention, the flexible sheet base can include a body portion and a tab extending from the body portion. The flexible separable layer can take the form of a mesh, a film, or a combination thereof. The portion of the flexible sheet base that extends out through the at least one open end of the chamber can include at least a portion of the tab. An elongate slit or opening can be disposed in the housing and can extend to the open end of the housing. The chamber can have a closed end opposite the open end and the housing can include a portion extending beyond the closed end of the chamber adapted for being gripped by a positioning device. The chamber can be generally cylindrical in shape.

In accordance with aspects of the present invention, the housing further can include an additional chamber adjacent the chamber and a divider wall disposed between the chamber and the additional chamber. The chamber and the additional chamber can each be cylindrical in shape. The chamber can include an opening in a side of the chamber opposite the divider wall. The opening can extend between two distal ends of the chamber, and the additional chamber comprises an opening in a side of the additional chamber opposite the divider wall and extending between two distal ends of the additional chamber. The implant can be removably disposed in the chamber and the additional chamber can be in a double-rolled configuration in which a first rolled portion of the implant is disposed in the chamber and a second rolled portion of the implant is disposed in the additional chamber. The implant can be continuous between the first rolled portion and the second rolled portion, and can pass external to the housing between the chamber and the additional chamber. The housing can be rigid. The flexible separable layer can be detachably and removably disposed on the body portion of the sheet. The implant can be in a single-rolled configuration or a double-rolled configuration.

In accordance with an example embodiment of the present invention, a deployment system is provided. The deployment system includes an elongate housing having a first end and a second end and including a partition extending at least partially between the first end and the second end. A first chamber can be formed in the housing on a first side of the partition and a second, chamber can be formed in the housing alongside the first chamber on a second side of the partition. The first chamber and the second chamber can extend to and can be open at the first end of the housing. A first elongate opening in the housing can provide side access into the first chamber. A second elongate opening in the housing can provide side access into the second chamber. A flexible implant including a flexible sheet base and a flexible separable layer can be removably disposed on the sheet base. A first rolled portion of the implant can be removably disposed in the first chamber, a second rolled portion of the implant can be removably disposed in the second chamber, and a third portion of the implant can pass external to the housing between the first chamber and the second chamber.

In accordance with an example embodiment of the present invention, a deployment system for a mesh or a film is provided. The flexible separable layer can take the form of a mesh, a film, or a combination thereof. The deployment system can include an elongate housing with a chamber formed therein. The elongate housing can have an elongate opening extending along a side thereof in such a way as to provide side access into the chamber. A flexible implant can be disposed in the chamber of the housing. The flexible implant can include a flexible sheet base and a flexible separable layer removably disposed on the flexible sheet base. The flexible implant can be removably disposed in the chamber of the housing in a rolled configuration. A portion of the flexible sheet base can extend out the elongate opening.

In accordance with further aspects of the present invention, the flexible sheet base can include a body portion and a tab extending from the body portion. The flexible separable layer can be removably disposed on the body portion of the flexible sheet base. The portion of the flexible sheet base that extends out through the elongate opening can include at least a portion of the tab. The chamber can have two ends and can be closed at one of the two ends. An end cap can be removably disposed on one of the two ends of the housing. Removal of the end cap can open one of the two ends of the chambers and can provide access into the chamber. The portion of the flexible sheet base extending out the elongate opening can extend beyond the housing in an amount capable of being gripped by a user.

In accordance with an example embodiment of the present invention, a flexible implant is provided. The flexible implant can include a flexible sheet base having a body portion and a tab extending from the body portion at an end of a width of the flexible sheet base. The flexible implant can include a flexible separable layer having a first major surface and a second major surface opposite the first major surface. The flexible separable layer can be removably disposed at least on the body portion of the flexible sheet base in such a way that the first major surface is contiguous with the flexible sheet base. The flexible implant can be disposed in a rolled configuration that includes one or two rolls each being aligned on a central axis that is substantially perpendicular to the width of the flexible sheet base. The flexible sheet base can be adapted to independently assume a rolled shape subsequent to unrolling the flexible implant, placing the second major surface of the flexible separable layer against a target site, and releasing the flexible implant, thereby causing the flexible sheet base to separate from the flexible separable layer. The flexible implant can be in a single-rolled configuration including only one roll or a double-rolled configuration including only two rolls.

BRIEF DESCRIPTION OF THE FIGURES

These and other characteristics of the present invention will be more fully understood by reference to the following detailed description in conjunction with the attached drawings, in which.

DETAILED DESCRIPTION

Figure 1:
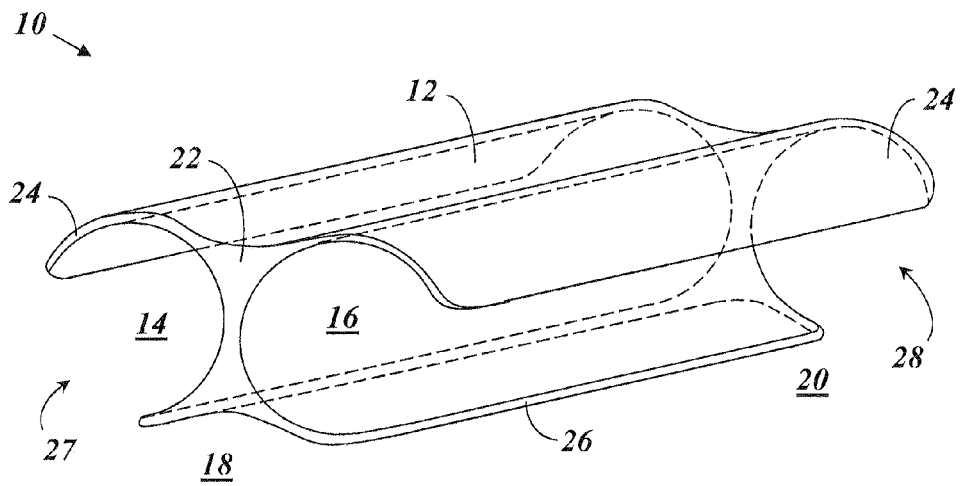
FIG. 1 is a perspective view of a deployment device having two chambers, according to an example embodiment of the present invention.

An illustrative embodiment of the present invention relates to a deployment device for a flexible implant. The deployment device can include a housing and one or two chambers (e.g., cylindrical in shape), which are each open at an end of the housing and adapted to receive a rolled flexible implant or a rolled portion of a flexible implant. In embodiments of the deployment device having two chambers, the flexible implant is rolled into a double-rolled configuration and placed in the two chambers of the housing in such a way that an exposed portion of the flexible implant is disposed external to the housing between two rolled portions disposed within the two chambers. In this way, the exposed portion of the flexible implant can be easily placed by a user (e.g., a surgeon) onto a target site prior to removing the remaining rolled portions of the flexible implant from the deployment device. In embodiments having a single chamber, the flexible implant can optionally include a tab and can have a length that is greater than a length of the chamber. The flexible implant can be rolled and inserted into the chamber of the housing in such a way that the tab extends out through an open end of the chamber and beyond the housing. The tab can be gripped for removal of the flexible implant from the deployment device and can be used for unrolling the flexible implant once removed from the housing of the deployment device.

In accordance with another illustrative embodiment of the present invention, a flexible implant is provided that is adapted to be easily and conveniently deployed and placed against a target site. The flexible implant can include a flexible base sheet having a body portion and a tab extending from the body portion. A flexible separable layer can be removably disposed on the body portion in such a way that the flexible separable layer is contiguous with (e.g., in contact with) the flexible base sheet. The flexible separable layer can take the form of a mesh, a film, or a combination thereof. The flexible implant can be rolled into a single-rolled or double-rolled configuration, with the flexible separable layer disposed on outward facing surface(s) of the resulting roll(s). The flexible implant can be placed against a target site such that the outward facing surface(s) of the roll(s), on which the flexible separable layer is disposed, are in contact with the target site. The flexible implant can be unrolled in such a way that spreads the flexible separable layer out against the target site. The flexible sheet base can be adapted in such a way that upon subsequently releasing the flexible implant (e.g., upon letting go of the flexible implant), the flexible sheet base independently assumes a rolled configuration (e.g., returns to the same rolled configuration in which it was earlier disposed). In contrast to this re-rolling of the flexible sheet base, the flexible separable layer can be adapted to remain disposed against the target site (e.g., in a substantially planar configuration or another configuration in which the flexible separable layer does not form one or more revolutions). Accordingly, in such illustrative embodiments, the re-rolling of the flexible sheet base is unmatched by the flexible separable layer, thereby causing the flexible sheet base to separate from the mesh film upon release thereof, subsequent to unrolling the flexible implant with the flexible separable layer against the target site.

FIGS. 1 through 12, wherein like parts are designated by like reference numerals throughout, illustrate example embodiments of a deployment device for use with a flexible implant according to the present invention. Although the present invention will be described with reference to the example embodiments illustrated in the figures, it should be understood that many alternative forms can embody the present invention. One of skill in the art will additionally appreciate different ways to alter the parameters of the embodiments disclosed, such as the size, shape, or type of elements or materials, in a manner still in keeping with the spirit and scope of the present invention.

Figure 2:
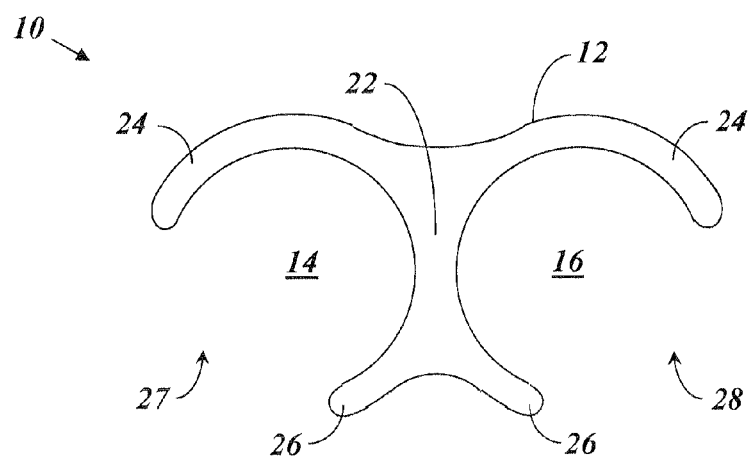
FIG. 2 is a cross-sectional view of the deployment device of FIG. 1, according to aspects of the present invention.

FIG. 1 depicts a perspective view of a deployment device 10 according to an example embodiment of the present invention. FIG. 2 further depicts the deployment device 10 from a cross-sectional view. The deployment device 10 includes an elongate housing 12 having a first end 18 and a second end 20. Formed in the housing 12 are a first chamber 14 and a second chamber 16. The first and second chambers 14, 16 are separated by a partition 22 (e.g., a divider wall) extending between the first and second ends 18, 20 of the housing 12. In the example embodiment of FIG. 1, the first and second chambers 14, 16 are disposed alongside one another in a generally parallel manner. The first and second chambers 14, 16 can have substantially the same dimensions (e.g., length, width, height, diameter, etc.). The first and second chambers 14, 16 can be generally cylindrical in shape, as illustrated in the example embodiment of FIG. 1, or can have any other suitable shape(s). In illustrative embodiments, the first and second chambers 14, 16 are mirror-images of one another. In alternative embodiments, the first and second chambers 14, 16 have shapes that are congruent with one another, geometrically similar to one another, or different from one another. Upon reading the present specification, one of skill in the art will appreciate a wide variety of ways to alter the shapes, dimensions, layouts of the first and second chambers 14, 16. All such alternatives and modifications are contemplated within the scope of the present invention. Any suitable shapes, dimensions, and layouts can be used to implement the present invention.

In accordance with illustrative embodiments of the present invention, both the first and second chambers 14, 16 extend to and are open at one of the first and second ends 18, 20 of the housing 12. In this way, access into the first and second chambers 14, 16 is provided through at least one of the first and second ends 18, 20. In the example embodiment of FIG. 1, the first and second chambers 14, 16 extend to and are open at both the first and second ends 18, 20 of the housing 12, such that access into the first and second chambers 14, 16 is provided at both the first end 18 and the second end 20 of the housing 12.

In addition to the first and second chambers 14, 16 both being open at the first and/or second ends 18, 20 of the housing 12, the first and second chambers 14, 16 each can be open along and accessible through an outer side of the housing 12. For example, in the example embodiment of FIG. 1, the housing 12 includes a first elongate opening 27 extending along a length of the first chamber 14 and disposed at an outer side of the first chamber 14 (i.e., a side that is generally opposite an inner side of the first chamber 14 abutting the partition 22). Furthermore, the first elongate opening 27 extends to the first end 18. As illustrated in FIG. 2, the inner wall of the first chamber 14 has a cross-sectional shape generally resembling a 'C'. Accordingly, when viewing the cross-section, the first elongate opening 27 is a space that separates the two points or tips of the C-shaped inner wall of the first chamber 14. Similarly, the second chamber 16 can be open along an outer side thereof. For example, in the example embodiment of FIG. 1, the housing 12 includes a second elongate opening 28 extending along a length of the second chamber 16 on an outer side of the second chamber 16 (i.e., a side that is opposite an inner side of the second chamber 16 abutting the partition 22). As illustrated in FIG. 2, the inner wall of the second chamber 16 has a cross-sectional shape generally resembling a 'C'. Accordingly, when viewing a cross-section of the deployment device 10, the second elongate opening 28 provides a space that separates the two points or tips of the C-shaped inner wall.

In addition to the partition 22, the inner walls of first and second chambers 14, 16 are defined by upper extensions 24 and lower extensions 26. In the example embodiment of FIG. 1 in which the first and second chambers 14, 16 are generally cylindrical in shape, the upper and lower extensions 24, 26 are generally arch-shaped.

In this way, the upper extensions 24, partition 22, and lower extensions 26 collectively form the generally C-shaped cross-section of each of the first and second chambers 14, 16, as depicted in FIG. 2.

It should be appreciated that the example cross-sectional shapes of the first and second chambers 14, 16 depicted in the figures (e.g., the "C" shapes) are provided herein only for purposes of illustration and clarity. These examples in no way limit the present invention. Upon reading the present specification, one of skill in the art will appreciate a variety of alternative shapes the first and second chambers 14, 16 can assume. All such alternatives and modifications are contemplated within the scope of the present invention. In general, the first and second chambers 14, 16 can be provided with any suitable shape (e.g., cross-sectional shape).

Figure 3:
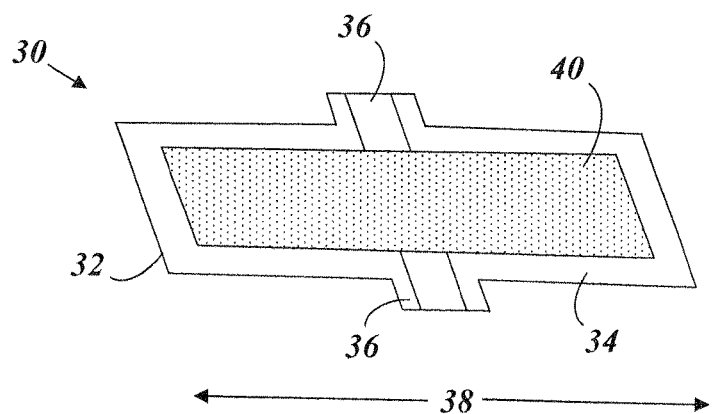
FIG. 3 is a perspective view of a flexible implant, according to aspects of the present invention.

FIG. 3 depicts a perspective view of a flexible implant 30 adapted for use with the deployment device 10, in accordance with an example embodiment of the present invention. The flexible implant 30 can include a flexible sheet base 32 having a body portion 34 and at least one tab 36 extending from the body portion 34. Each tab 36 can have a width that is less than a full width 38 of the flexible sheet base 32, as illustrated in FIG. 3. Furthermore, in the example embodiment of FIG. 3, the flexible sheet base 32 includes two such tabs 36 extending from opposite ends of the body portion 34. The body portion 34 can occupy a majority of the flexible sheet base 32, and the tab(s) 36 can extend from the body portion 34 at a center of the width 38 of the flexible sheet base 32. Alternatively, the tab(s) 36 can extend from the body portion 34 at other positions along the width 38 of the flexible sheet base 32.

The flexible sheet base 32 can be any suitable material, including polyethylene-based materials. For example, in illustrative embodiments, the flexible sheet base 32 is formed of polyethylene materials (e.g., spun-bound polyethylene). It should be appreciated that the invention is not limited to the illustrative example materials provided herein. Upon reading the present specification, one of skill in the art will appreciate a wide variety of other suitable materials that can be utilized. All such alternatives and modifications are contemplated within the scope of the present invention.

The flexible implant 30 further can include a flexible separable layer 40 removably disposed on the flexible sheet base 32 (e.g., disposed on and contiguous to with a surface of the flexible sheet base 32). For example, the flexible separable layer 40 can be a hernia repair mesh, an anti-adhesion barrier film, any other film or mesh, or equivalently any other suitable sheet-like prosthesis or bioabsorbable and/or biodegradable material. Optionally, the flexible separable layer 40 can adhere with the surface of the flexible sheet base 32 on which the flexible separable layer 40 is disposed. For example, in accordance with some embodiments of the present invention, a tie layer of adhesive material is included between the flexible sheet base 32 and the flexible separable layer 40 to provide adhesion between the flexible sheet base 32 and the flexible separable layer 40. Such a tie layer of adhesive material can be provided by disposing the adhesive material on the flexible sheet base 32 and subsequently placing the flexible separable layer 40 on the adhesive material. In accordance with other embodiments of the present invention, adhesion between the flexible sheet base 32 and the flexible separable layer 40 itself can be established by adhesive materials or layers included in the flexible separable layer 40. For example, the flexible separable layer 40 can include a coating, an adhesive layer, or other adhesive features adapted to bond with the flexible sheet base 32 once placed in contact with a surface of the flexible sheet base 32. In one illustrative embodiment, the flexible separable layer 40 includes a mesh with a side that is coated with an omega-3 fatty acid based material which, when laid on the flexible sheet base 32, creates a suitable adhesion from surface tension developed between itself and the flexible sheet base 32. In some embodiments, the flexible sheet base 32 includes a low-density polyethylene coating which can improve the surface tension developed between itself and the flexible separable layer 40 and thereby improve the adhesion therebetween. In accordance with some embodiments of the present invention, some adhesion between the flexible sheet base 32 or the flexible separable layer 40 is produced or enhanced by pressing together the flexible sheet base 32 and the flexible separable layer 40. Alternatively, the adhesion could result from application of heat, or as a part of a cooling from a curing process of the flexible separable layer 40 while in contact with the flexible sheet base 32. Upon reading the present specification, one of skill in the art will appreciate yet other ways to provide suitable adhesion between the flexible sheet base 23 and the flexible separable layer 40 in a manner enabling the flexible separable layer 40 to be removably disposed on the flexible sheet base 32. All such alternatives and modifications are contemplated within the scope of the present invention.

In all such embodiments where the flexible separable layer 40 adheres to the flexible sheet base 32, the flexible separable layer 40 can be removable from the flexible sheet base 32 (e.g., by breaking the adhesive bonds) in a manner that does not result in partial or complete destruction of the flexible separable layer 40. As such, the separable layer is separable, detachable, and/or removable, as such terms are utilized herein.

In general, the flexible separable layer 40 can occupy the same area or less area as the flexible sheet base 32. The flexible separable layer 40 generally can be removably disposed onto only the body portion 34 of the flexible sheet base 32, or can be removably disposed onto the body portion 34 and some/all of the tab(s) 36. In the example embodiment of FIG. 3, the flexible separable layer 40 is removably disposed onto the body portion 34 of the flexible sheet base 32 and not on either of the two tabs 36. Additionally, in the example embodiment of FIG. 3, the flexible separable layer 40 occupies less area than the body portion 34 of the flexible sheet base 32.

Figure 4:
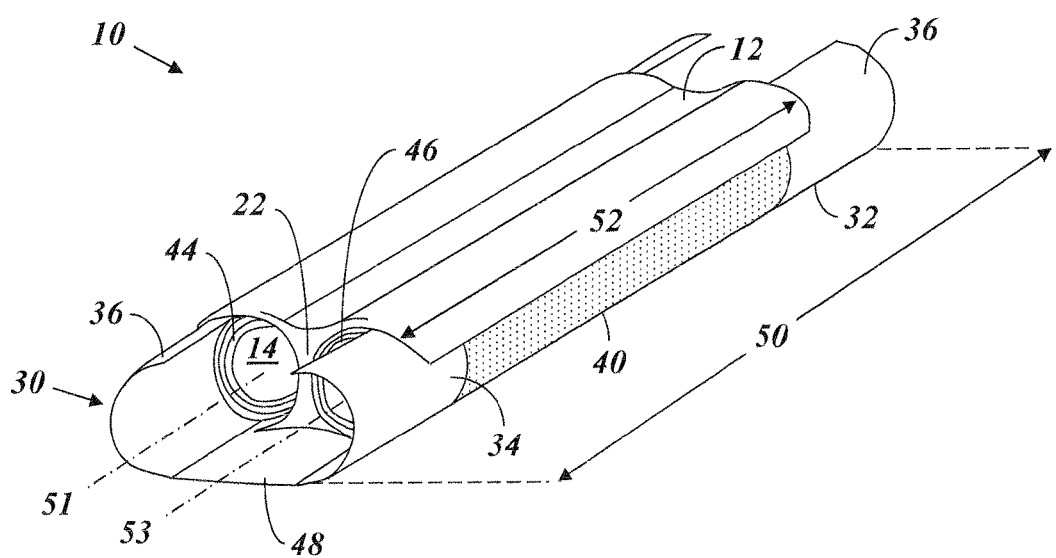
FIG. 4 is a perspective view of the deployment device of FIG. 1 with the flexible implant of FIG. 3 disposed therein, according to one aspect of the present invention.

The flexible implant 30 is adapted to be releasably received by and removably disposed within the first and second chambers 14, 16 of the deployment device 10 in a double-rolled configuration (i.e., forming two rolls of material), as depicted in FIG. 4. The double-rolled configuration can be produced by gripping the two sides of the flexible implant 30 at the ends of the width 38 and rotating each side inward toward the center of the width 38. In illustrative embodiments, this forms the double-rolled configuration with a first rolled portion 44, a second rolled portion 46, and a third portion 48 extending between the first and second rolled portions 44, 46. The first and second rolled portions 44, 46 can disposed on the same surface of the flexible implant 30 as illustrated, such that their cross-sections collectively resemble a 'B'-shaped scroll (e.g., a binocular shape) more closely than an 'S'-shaped scroll. In the example embodiment of FIG. 4, the third portion 48 extends along a full length of the flexible implant 30 in the double-rolled configuration. Furthermore, as illustrated in FIG. 4, when the flexible implant 30 is removably disposed in the first and second chambers 14, 16, the first rolled portion 44 is disposed in (e.g., fully occupies) the first chamber 14, the second rolled portion 46 is disposed in (e.g., fully occupies) the second chamber 16, and the third portion 48 between the first and second rolled portions 44, 46 is disposed external to the housing 12 of the deployment device 10 and held in place against (i.e., contiguous and in contact with) the lower extensions 26 of the housing 12. In illustrative embodiments, the flexible implant 30 is rolled to form two rolls such that the flexible separable layer 40 is disposed on outward-facing surfaces of the two rolls. Accordingly, in such illustrative embodiments, the flexible separable layer 40 is disposed on an outward facing surface of the third portion 48 when the flexible implant 30 is loaded into the deployment device 10. In this way, the flexible separable layer 40 is exposed on the third portion 48 and disposed external to the housing 12.

In illustrative embodiments of the present invention, the first and second rolled portions 44, 46 are formed of equal amounts of the flexible implant 30 and make the same number of revolutions (e.g., turns), such that the third portion 48 therebetween is a central portion of the flexible implant 30 which includes at least a portion of the tab(s) 36. This is shown in the example embodiment of FIG. 4. In alternative embodiments, the tab(s) 36 can be displaced away from the center of the width 38 and the first and second rolled portions 44, 46 can be formed of different amounts of the flexible implant 30, such that the third portion 48 includes a non-central portion of the flexible implant 30 at which at least a portion of the tab(s) 36 are disposed. For illustrative embodiments of the deployment device 10 in which the flexible sheet base 32 includes at least one tab 36, the double-rolled configuration is formed such that the third portion 48 is a portion of the flexible implant that includes at least a portion of the tab 36.

In illustrative embodiments of the deployment device 10 in which the flexible sheet base 32 includes at least one tab 36, the tab 36 is sized such that neither side at either end of the width of the tab 36 makes a full revolution (i.e., 360 degrees) when the flexible implant 30 is disposed in the housing 12 in the double-rolled configuration. For example, as depicted in the embodiment of FIG. 4, the sides at each end of the width of the tabs 36 each make about a 180 degree revolution. In this way, each tab 36 avoids doubling over itself in a manner that would produce surface contact between two portions of the tab 36 when the flexible implant 30 is in the double-rolled configuration. The present invention can provide that each tab 36 form less than a full revolution. In particular, after the deployment device 10 is positioned at the target area, the tab 36 can be grasped on its top and bottom ends by a user (e.g., using graspers to hold the flexible implant 30 in place) without impeding or preventing the unrolling of the flexible implant 30. Stated differently, certain illustrative embodiments of the present invention are based on a recognition that if the tab 36 included more than a single revolution, then grasping multiple revolutions of the tab 36 would result in multiple revolutions of the entire flexible implant 30 being held together, thereby making it impossible to fully unroll the flexible implant 30. Thus, in accordance with certain further aspects of the present invention, the tab 36 optionally can be sized such that the tab 36 is not doubled-over (e.g., is not overlapping itself at portions designed or intended to be grasped) when the flexible implant 30 is rolled and loaded into the deployment device 10. As yet a further benefit, providing no more than a single revolution of the tab 36 when the flexible implant 30 is loaded in the deployment device 10 in a rolled configuration can enable the flexible implant 30 to achieve a smaller outer diameter when in the rolled configuration, thereby permitting the flexible implant 30 to be used and adapted with smaller cannulas, for example. Furthermore, such a feature of the tab 36 having no more than a full revolution when the flexible implant 30 is in a rolled configuration and loaded in the deployment device 10 provides one less mechanism or feature with a potential to fail during use (e.g., due to misuse by a user, etc.).

In accordance with illustrative embodiments of the present invention, the flexible implant 30 in the double-rolled configuration longitudinally spans more distance than the longer of the first and second chambers 14, 16. More specifically, in illustrative embodiments, a longitudinal dimension of the first rolled portion 44 along its central axis 51 is greater than a longitudinal dimension of the first chamber 14 that is generally parallel to the central axis of the first rolled portion 44 when disposed therein. Furthermore, in such illustrative embodiments, a longitudinal dimension of the second rolled portion 46 along its central axis 53 is greater than a longitudinal dimension of the second chamber 16 that is generally parallel to the central axis of the second rolled portion 46 when disposed therein. In the example embodiment of FIG. 4, the flexible implant 30 when disposed in the housing 12 in the double-rolled configuration has a length 50 that is greater than a length 52 of the first and second chambers 14, 16. Accordingly, each tab 36 extends out the first end 18 of the housing 12 or the second end 20 of the housing 12, as depicted in the example embodiment of FIG. 4. This allows the tab(s) 36 to be gripped easily by a user (e.g., a surgeon) for facilitating removal of the flexible implant 30 from the housing 12 of the deployment device 10, as described in greater detail herein.

Figure 5:
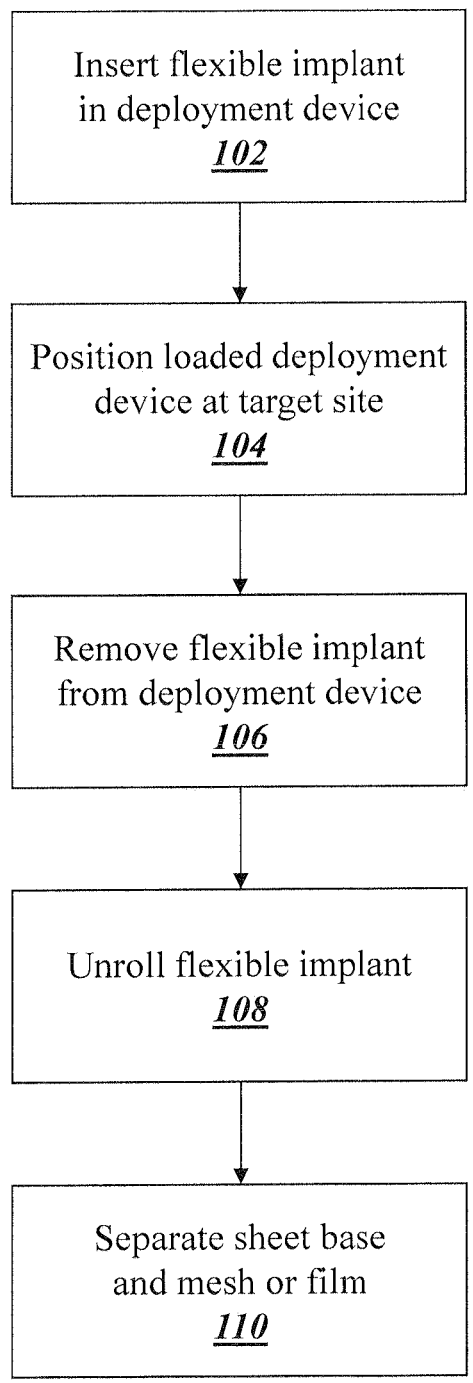
FIG. 5 is a flow chart of a method for using a deployment device, according to an example embodiment of the present invention.

FIG. 5 depicts an example embodiment of a method for using the deployment device 10. The flexible implant 30 can be rolled into the double-rolled configuration (by rolling each of the sides of the flexible implant 30 inward), and the flexible implant 30 can be inserted into the deployment device 10 in the double-rolled configuration (step 102), as depicted in FIG. 4. The loaded deployment device 10 can be positioned at a target site (step 104), e.g., a site of a hernia or other anatomical defect. For example, the loaded deployment device 10 can be advanced through one or more trocars to the target site, as would be appreciated by one of skill in the art upon reading the present specification. In embodiments having both the first and second chambers 14, 16, step 104 of positioning the loaded deployment device at the target site can include placing the exposed third portion 48 of the flexible separable layer 40 on the target site. In particular, the exposed third portion 48 can lowered from above toward the anatomical defect until the exposed portion of the flexible separable layer 40 is in contact with the defect site. For example, if the target site is a site of an abdominal hernia, a user can position the loaded deployment device in such a way that the exposed third portion 48 of the flexible separable layer 40 is pressed against the torn abdominal wall. In this way, the deployment device 10 can be used to carefully place the exposed third portion 48 of the flexible separable layer 40 while the deployment device 10 is still loaded with the flexible implant 30 (i.e., prior to removing the first and second rolled portions 44, 46 from the first and second chambers 14, 16).

Figure 9:
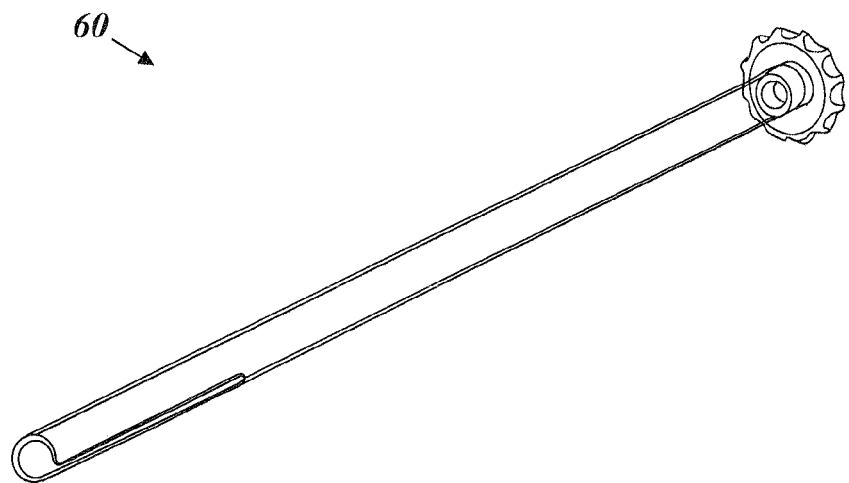
FIG. 9 is a perspective view of a removal device, according to aspects of the present invention.

Once suitably positioned at the target site, the flexible implant 30 can be removed from the deployment device 10 (step 106). For example, step 106 can be performed by a user manipulating one or more graspers to hold the tab 36 in place while gripping and pulling on the housing 12 away from the flexible implant 30 to retract the deployment device 10 and thereby remove the flexible implant 30 from the deployment device 10. Upon the flexible implant 30 being removed from the deployment device 10 (e.g., by holding the tab 36 in place and retracting the deployment device 10), the now-fully exposed flexible implant 30 can be unrolled (step 108). For example, step 108 can include a user manipulating one or more graspers to unroll each of the first and second rolled portions 44, 46. In illustrative embodiments, the strength of the coupling or adhesion between the sheet base 32 and the flexible separable layer 40 is sufficiently low that the act of rolling and unrolling the flexible implant 30 causes the flexible sheet base 32 and the flexible separable layer 40 to unfurl and/or re-furl separately and partially separate (e.g., at the edges) upon the flexible implant 30 being unrolled in step 108. Once unrolled (and/or while unrolling), the sheet base 32 and the flexible separable layer 40 can be separated (step 110). For example, step 108 can be performed by a user gripping the tab 36 and pulling (e.g., peeling) the sheet base 32 off the flexible separable layer 40. Notably, in step 110, the flexible separable layer may be partially positioned, e.g., if the exposed third portion 48 of the flexible separable layer 40 were placed into an operational position on the target site in step 104. Once separated from the sheet base 32, the flexible separable layer 40 can be fully placed against or on the target site, as would be appreciated by one of skill in the art upon reading the present specification. However, in illustrative embodiments of the present invention, the flexible separable layer 40 is completely applied by the time the flexible sheet base 32 is separated from the flexible separable layer 40 in step 110. The sheet base 32 can be removed from the target site using a removal device. For example, FIG. 9 depicts one suitable removal device 60, according to an example embodiment of the present invention.

The flexible sheet base 32 can be formed of a material that exhibits a tendency (e.g., a slight tendency) to remain in the rolled configuration after being unrolled in step 108. In such embodiments, the act of unrolling the flexible implant 30 in step 108 and subsequently letting go of the flexible implant 30 (and thereby releasing the holding force or rolling force imposed on the flexible implant 30 when unrolling in step 108) can cause a portion of the flexible sheet base 32 to re-furl and re-assume a rolled or partially rolled configuration. In illustrative embodiments, this re-furling or re-rolling of the flexible sheet base 32 is unmatched by the flexible separable layer 40. Rather, in illustrative embodiments, the flexible separable layer 40 (upon release of the holding force or rolling force applied to the flexible implant 30 in step 108) instead can remain adhered to the target site, e.g., as previously applied thereto. Accordingly, in such embodiments and illustrative implementations, the flexible sheet base 32 experiences more rerolling than the flexible separable layer 40, thereby causing the flexible sheet base 32 to partially or completely separate from the flexible separable layer 40 during such re-rolling motion.

Figure 6:
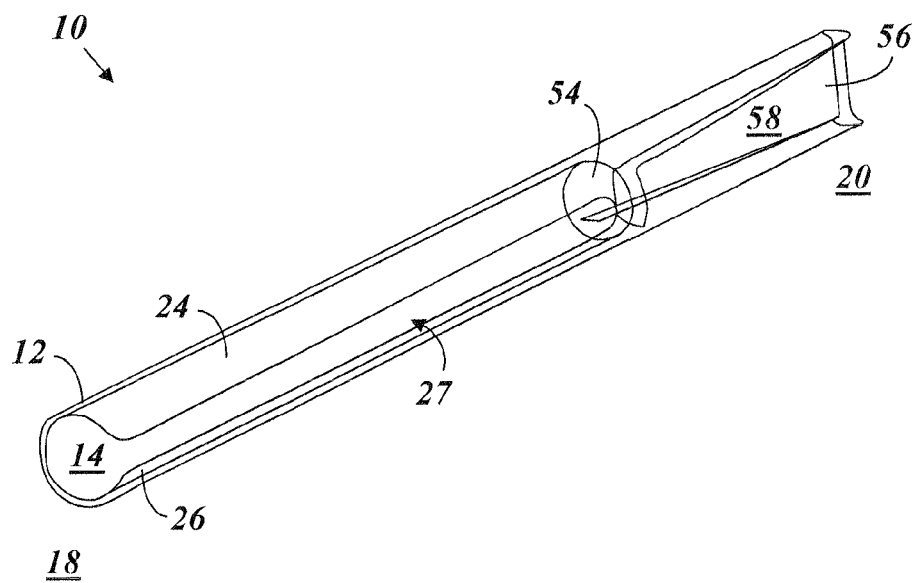
FIG. 6 is a perspective view of a deployment device having a single chamber, according to an example embodiment of the present invention.

In some embodiments, the deployment device 10 includes only a single chamber formed therein. For example, FIG. 6 depicts the deployment device 10 including only the first chamber 14, in accordance with an example embodiment of the present invention. In the example embodiment of FIG. 6, the first chamber 14 extends to and is open at the first end 18 of the housing 12. In this embodiment, the first chamber 14 does not extend to and is not open at the second end 20 of the housing 12. Rather, the first chamber 14 terminates at a wall 54. On the side of the wall 54 opposite the side at which the first chamber 14 is disposed, the housing 12 includes a grip extension 56. The grip extension 56 can include one or more substantially flat surfaces 58 suitable for being gripped by one or more graspers or other positioning devices when positioning the deployment device 10 to a target site.

As with the example embodiment of FIGS. 1 and 2, the deployment device 10 of FIG. 6 includes the first elongate opening 27 disposed in an outer side of the housing 12 and providing side access into the first chamber 14. Furthermore, as with the example embodiment of FIGS. 1 and 2, the first elongate opening 27 extends to the first end 18. In some alternative embodiments of the deployment device 10 wherein a single chamber is formed in the housing 12, there is no elongate opening disposed in an outer side of the housing 12. In such alternative embodiments, the inner wall of the first chamber 14 has a cross-section that is generally circular in shape. As illustrated, the deployment device 10 of the example embodiment of FIG. 6 does not include the partition 22.

Figure 7:
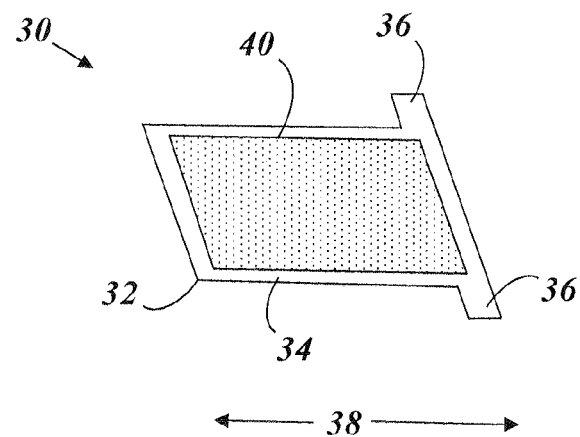
FIG. 7 is a perspective view of a flexible implant for use with the deployment device of FIG. 6, according to aspects of the present invention.
Figure 8:
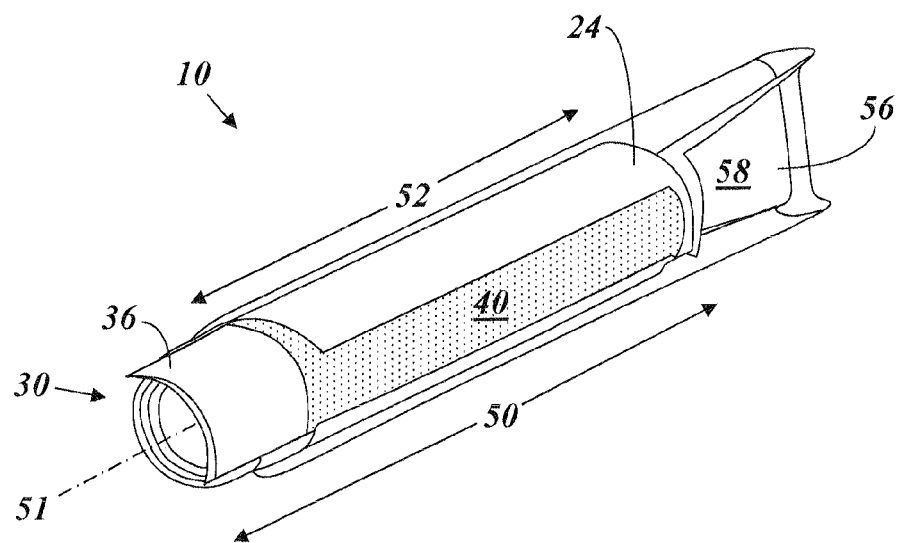
FIG. 8 is a perspective view of a deployment device having a single chamber with a mesh prosthesis disposed therein in a single-rolled configuration.

FIG. 7 depicts the flexible implant 30 adapted for use with the deployment device 10 of FIG. 6. In particular, the body portion 34 of the flexible sheet base 32 (upon which the flexible separable layer 40 is removably disposed) includes the tabs 36. Unlike the flexible implant 30 of FIG. 3, the tabs 36 are disposed at an end of the width 38 of the flexible implant 30. Although two tabs 36 are included in the example embodiment of FIG. 7, it should be appreciated that more or less tabs 36 alternatively can be included (e.g., just a single tab disposed at an end of the width 38 of the flexible implant 30). The flexible implant 30 of FIG. 7 can be rolled into a single-rolled configuration and loaded into the deployment device. For example, FIG. 8 depicts the deployment device 10 having only the first chamber 14 with the flexible implant 30 of FIG. 7 loaded therein in such a single-rolled configuration. As shown, the flexible implant 30 is disposed in the first chamber 14 in a single-rolled configuration (i.e., forming only a single roll of material). In the example embodiment of FIG. 8, the sheet base 32 includes only a single tab 36 which extends out the first end 18 of the housing 12, and which preferably forms less than a full revolution (i.e., less than 360 degrees). In the example embodiment of FIG. 8, the flexible implant 30 spans more distance longitudinally when disposed in the first chamber 14 in the rolled configuration than does the first chamber 14. Stated differently, the length 50 of the flexible implant 30 in the single-rolled configuration is greater than a length of the first chamber 14. More specifically, a longitudinal dimension of the flexible implant 30 in the single-rolled configuration along its central axis is greater than a longitudinal dimension of the first chamber 14 that is generally parallel to the central axis of the first rolled portion 44 when disposed therein. In the example embodiment of FIG. 8, there is no elongate exposed portion (e.g., such as the third portion 48 of the deployment device 10 of FIG. 4) of the flexible separable layer 40 which is disposed external to the housing 12, other than any optional portion of the flexible separable layer 40 removably disposed on the tab 36. In some embodiments, a portion of the flexible sheet base 32 (e.g., a portion of the flexible sheet base 32 disposed at an end of the width 38 of the flexible sheet base 32) extends out through the first elongate opening 27. In such embodiments, the flexible separable layer 40 can be disposed on the exposed portion of the flexible sheet base 32 or can be only on portions of the flexible sheet base 32 that do not extend out the first elongate opening 27. Such a portion of the flexible sheet base 32 extending out of the housing 12 through the first elongate opening 27 can be useful in providing an additional area that can be gripped by a user (e.g., surgeon) when manipulating the flexible implant 30 at a target site (e.g., in a patient).

The deployment device 10 of the example embodiment of FIG. 6 can be used and operated in substantially the same manner described previously herein with reference to FIG. 5. In particular, the flexible implant 30 can be inserted into the deployment device 10 in the single-rolled configuration (step 102). The loaded deployment device 10 then can be positioned at a target site (step 104), e.g., by passing the loaded deployment device 10 through one or more trocars. Once positioned at the target site, the flexible implant 30 can be removed from the deployment device 10 (step 106), e.g., by holding the tab 36 in place and retracting the deployment device 10 to remove and fully expose the flexible implant 30 in the single-rolled configuration. The fully exposed flexible implant 30 can be unrolled (step 108). Subsequent to or during unrolling of the flexible implant 30, the sheet base 32 and the flexible separable layer 40 can be separated from one another (step 110). Once separated from the sheet base 32, the flexible separable layer 40 can be placed against or on the target site, as would be appreciated by one of skill in the art upon reading the present specification. The sheet base 32 can be removed from the target site (e.g., removed from the patient), using the removal device 60 of FIG. 9.

As should be understood by those of skill in the art upon study of the present disclosure, the flexible implant 30 can be packaged and sold preloaded in the deployment device 10 and can be used as a reloadable cartridge as part of a larger manipulating device. Rolled up inside the deployment device 10, the flexible implant 30 is easily inserted to a target site (e.g., within a patient), whereas on its own such a flexible implant 30 would typically fold and buckle in an undesired manner. Furthermore, once positioned at the target site (e.g., inside the patient), the flexible implant 30 can be placed on the target site as the rolls are unrolled in small sections, while the remainder of the flexible implant 30 remains unexposed and rolled up in the sheet base 32. This provides a user with greater visibility of the work space (e.g., surgical field) and allows for more accurate placement of the flexible separable layer 40. In addition, during insertion, unplaced portions of the flexible separable layer 40 remain protected from bodily fluids and mechanical disruption inside of the roll(s) of the flexible implant 30. These forms of protection can be of great importance when handling such flexible separable layers 40 (or other such sheet-like materials) which can be delicate, can have self-adhering layers, and/or can be loaded with therapeutic agents.

Additionally, in certain illustrative embodiments of the deployment device 10 having both the first and second chambers 14, 16, the deployment device 10 and flexible implant 30 can be adapted such that a portion of the flexible separable layer 40 is exposed and disposed external to the housing 12. This allows a user (e.g., a surgeon) to place a portion of the flexible separable layer 40 at the target site before removing and exposing a remainder of the flexible separable layer 40 from the first and second chamber 14, 16. Beneficially, fixing an initial portion of the flexible separable layer 40 in this manner can allow a surgeon to achieve greater accuracy when placing the flexible separable layer 40 at the target site and easier manipulation of the flexible separable layer 40. As generally described previously herein, many such flexible separable layers 40 tend to fold or buckle, which can produce undesired self-adhering. Accordingly, placing (e.g., and optionally affixing) an initial exposed portion of the flexible separable layer 40 disposed an outward-facing surface of the third portion 48 of the flexible implant 30 onto a target site prior to exposing and placing a remainder of the flexible separable layer 40 can be useful in preventing the flexible separable layer 40 from bending or folding over (e.g., and adhering to itself). In embodiments of the deployment device 10 including only the first chamber 14, the tab 36 on the sheet base 32 extending external to the housing 12 provides a user with an easy mechanism for gripping and manipulating the flexible implant 30 (e.g., holding the flexible implant 30 in place, removing the flexible implant 30 from the deployment device 10, unrolling the flexible implant 30, etc.).

Accordingly, embodiments of the present invention can provide users with greater handling capabilities and easier deployment of such flexible separable layers 40 (or any other sheet-like material), for example during laparoscopic repair and/or other medical or surgical applications. Furthermore, the flexible sheet base 32 (on which the flexible separable layer 40 is removably disposed, e.g., during insertion of the flexible separable layer 40 into the body and when initially removed from the deployment device 10 at the target site) can provide additional protection to the target site, e.g., by providing an additional barrier between the target site and the graspers used in deployment. For example, in medical applications, this can reduce the likelihood of the graspers inadvertently tearing or otherwise damaging internal body organs when deploying and applying the flexible separable layer 40 to the surface of internal body organs. Furthermore, for example, the flexible sheet base 32 can have mechanical integrity as well as tear and puncture resistant, which additionally can protect the flexible separable layer 40 from destructive forces. For example, by providing a tab 36 that can be grasped during removal of the flexible implant 30 from the deployment device 10, it is possible to avoid placing additional surface tension on the flexible separable layer 40, thereby assisting in preserving the integrity of the flexible separable layer 40 (e.g., which can be more susceptible to rips, tears, or other structural damage).

Furthermore, once removed from the deployment device 10 at the target site, the flexible implant 30 can be placed on the target site as appropriate by unrolling the flexible implant 30 in such a way that the roll(s) of the flexible implant 30 formed by the rolled configuration are rolled out onto the target site (with the flexible separable layer 40 facing the target site and the flexible sheet base 32 facing away from the target site). In this way, the flexible separable layer 40 optionally can be rolled out and placed on the target site in a single, simultaneous step. Beneficially, when applied and implemented for medical and/or surgical applications, optionally combining these steps can enable a surgeon to achieve shorter surgery times. Furthermore, the simultaneous act of unrolling the flexible implant 30 can include pressing the flexible implant 30 into (e.g., and smoothing it out onto) the target site in such a way that the flexible separable layer 40 comes into contact with (e.g., and adheres with) the target site. In some instances and implementations, this act of pressing the flexible implant 30 into the target site and smoothing it across the target site can be achieved by a user using a grasper and pressing (e.g., with sweeping motions) on the side of the flexible implant 30 on which the flexible sheet base 32 is disposed. Stated differently, the flexible implant can be, e.g., lowered onto the target site with the flexible separable layer 40 "face down" against the target site. The graspers then can be used to unroll the flexible implant 30 and press against flexible sheet base 32, which is "face up" on the target site, thereby smoothing the surface of the flexible separable layer 40 against the target site and ensuring proper physical contact (e.g., and hence also adhesion/bonding) between the target site and the flexible separable layer 40 prior to removing the flexible sheet base 32 from the flexible separable layer 40. Thus, in this way, the flexible separable layer 40 beneficially can be placed on the target site (e.g., in step 108) without the user ever physically touching the flexible separable layer 40 with the graspers. The graspers thus can apply a smoothing force against the target site, and can be used to urge the flexible separable layer 40 into contact with the target site (e.g., the tissue) in a manner that neither damages the flexible separable layer 40 nor compromises adequate placement/physical contact of the flexible separable layer 40 against the target site. Accordingly, in such illustrative usages, when the flexible sheet base 32 is separated from the flexible separable layer 40 in step 110, the flexible separable layer 40 has already been applied to the target site.

Furthermore, once removed from the flexible sheet base 32, the flexible separable layer 40 optionally can independently assume a contoured three-dimensional shape adapted to provide greater treatment/reinforcement at the target site and/or adapted to better adhere to the target site. Accordingly, in illustrative embodiments, the flexible separable layer 40 is rolled into the rolled configuration in a manner that does not compromise the ability of the flexible separable layer 40 to unroll and assume a predetermined three-dimensional shape. Upon reading the present specification, one of skill in the art will appreciate yet further benefits and advantages not explicitly described herein.

In general, any suitable flexible separable layer 40 can be utilized. For example, any suitable uncoated mesh, or coated mesh (e.g., having a tissue-adherent coating) may be used. As further examples, any suitable hernia repair mesh, any suitable anti-adhesion barrier film, any other suitable film or mesh, or equivalently any other suitable sheet-like prosthesis or bioabsorbable and/or biodegradable material may be utilized with embodiments of the present invention. Upon reading the present specification, one of skill in the art will appreciate a wide variety of additional flexible separable layers 40 that can be utilized. All such alternatives and modifications to the embodiments described herein are contemplated within the scope of the present invention. The present invention is not limited to any specific examples, which are provided herein for purposes of clarity and illustration.

Figure 10A:
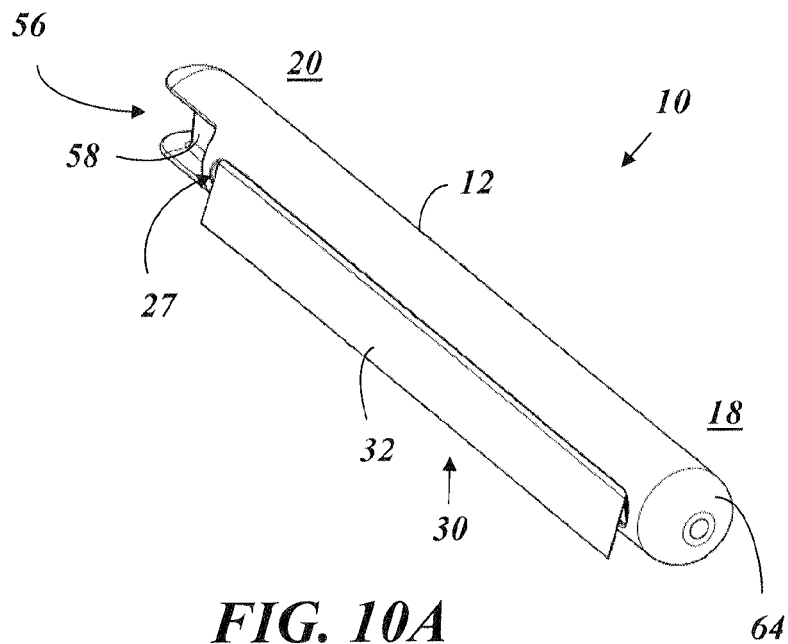
FIG. 10A is a perspective view of a deployment device having a single chamber and two closed ends, according to an example embodiment of the present invention.
Figure 10B:
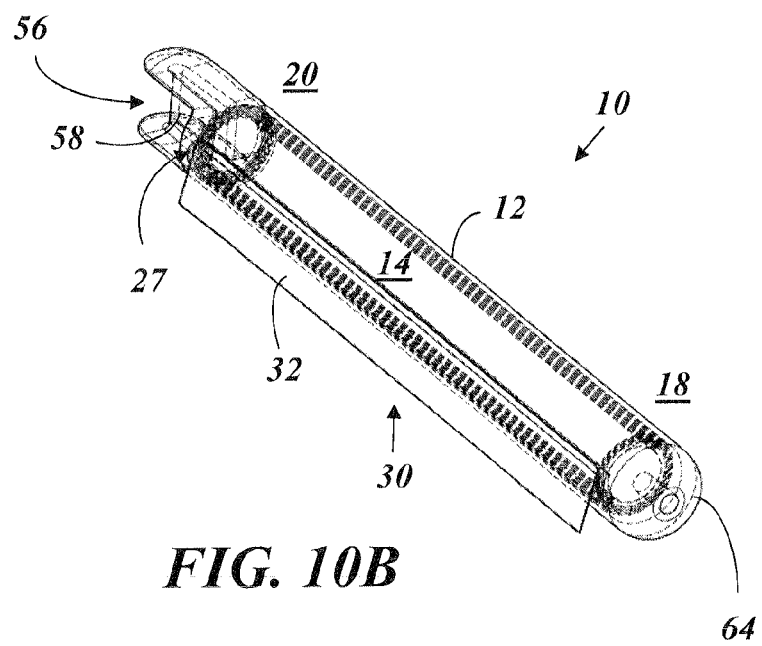
FIG. 10B is a transparent perspective view of the deployment device of FIG. 10A, according to aspects of the present invention.

In accordance with an alternative embodiment of the present invention, the deployment device 10 can include just a single chamber that is closed at both of its ends. For example, FIGS. 10A and 10B depict perspective views of the deployment device 10 including only the first chamber 14, in accordance with an example embodiment of the present invention. In the example embodiment of FIGS. 10A and 10B, each of the first chamber 14 and the housing 12 are generally cylindrical in shape, with the first elongate opening 27 extending between the first and second ends 18, 20 of the housing 12 and along at least a portion of a length of the first chamber 14. As depicted, the housing 14 is closed at both the first and second ends 18, 20. In particular, in the example embodiment of FIGS. 10A and 10B, an end cap 64 is disposed at (e.g., removably coupled to, formed integral with, etc.) the housing 14 at the first end 18. Accordingly, in the example embodiment of FIGS. 10A and 10B, access into the first chamber 14 is provided exclusively by the first elongate opening 27. In embodiments where the end cap 64 is removable from and re-attachable to the housing 12 in an operational manner (e.g., not requiring destructive forces), removing the end cap 64 from the housing 12 can open the first end 18 of the housing 12 and thereby provide access into the first chamber 14, for example, for enabling the flexible implant 30 to be inserted therein in a single-rolled configuration.

As illustrated in the example embodiment of FIGS. 10A and 10B, the flexible implant 30 can be disposed in the first chamber 14. The flexible implant 30 of FIGS. 10A and 10B does not include any such tab 36 as described and depicted previously herein with reference to FIGS. 1 through 9. As illustrated in FIGS. 10A and 10B, a segment of the body portion 34 of the flexible sheet base 32 (specifically, a segment that is disposed at an end of the width 38 of the flexible sheet base 32) extends out through the first elongate opening 27 and beyond the housing 12 in an amount capable (e.g., and suitable) of being gripped by a user, for example using one or more graspers. However, in alternative embodiments of the present invention, the flexible sheet base 32 includes one or more tabs 36 (e.g., occupying less than the full width 38 of the flexible sheet base 32) extending out through the first elongate opening 27 and beyond the housing 12 in an amount capable (e.g., and suitable) of being gripped by a user, for example using one or more graspers. When implemented for embodiments in which the housing 12 is closed at its first and second ends 18, 20, tab(s) 36 can be disposed at end(s) of the width 38 of the flexible sheet base 32 (as depicted in the example embodiment of FIG. 7), or can be disposed elsewhere along the width 38 of the flexible sheet base 32.

Figure 11A:
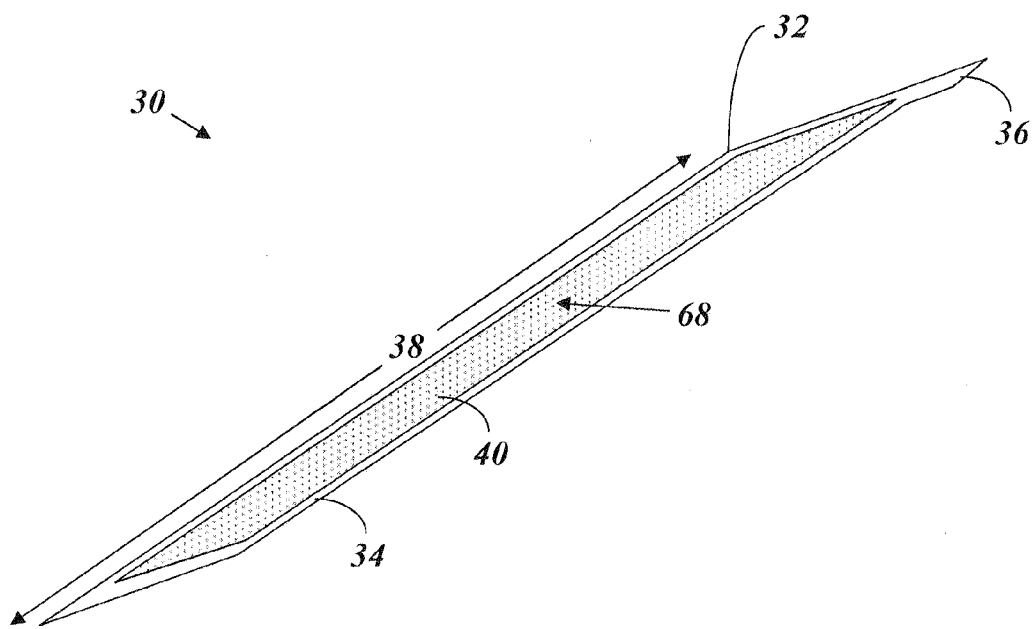
FIG. 11A is a perspective view of a flexible implant in an unrolled, substantially flat configuration, according to an example embodiment of the present invention.
Figure 11B:
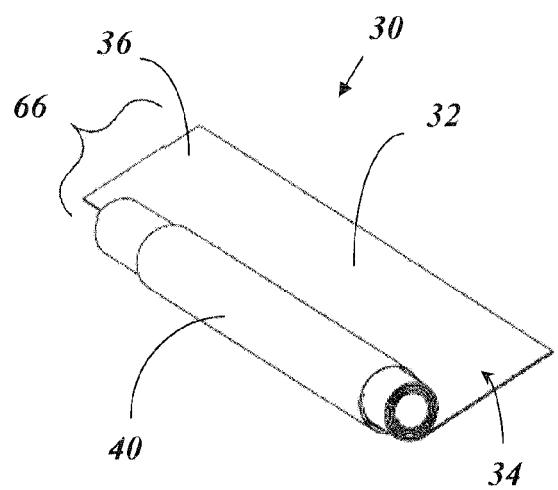
FIG. 11B is a perspective view of the flexible implant of FIG. 11A in a single rolled configuration, according to aspects of the present invention.

In accordance with some example embodiments of the present invention, the flexible prosthesis 30 is provided in absence of the deployment device 10. For example, FIG. 11A depict the flexible prosthesis in an unrolled, substantially flat configuration, in accordance with an example embodiment of the present invention. As illustrated, the flexible prosthesis 30 includes the flexible sheet base 32 having the body portion 34 and at least one tab 36. In the example embodiment of FIG. 11A, tab 36 extends from an end of the width 38 of the flexible sheet base 32 and occupies less than the full width 38 of the body portion 34. Stated differently, the tab 36 has a width that is less than the width 38 of the flexible sheet base 32. Removably disposed on at least the body portion 34 is the flexible separable layer 40. The flexible separable layer 40 includes a first major surface (hidden from view in FIGS. 11A and 11B) and a second major surface 68 opposite the first major surface. The first major surface is contiguous with (in contact with) the flexible sheet base 32. As described previously herein, the flexible separable layer 40 can be any suitable flexible separable layer 40, including, as non-limiting examples, a hernia repair mesh, an anti-adhesion barrier film, any other film or mesh, or equivalently any other suitable sheet-like prosthesis or sheet-like bioabsorbable and/or biodegradable material. As depicted in FIG. 11B, the flexible implant 30 can be rolled into a single-rolled configuration.

In accordance with illustrative embodiments (e.g., including the example embodiment of FIG. 11B), when in the single-rolled configuration, a portion 66 of the flexible implant 30 at an end of the width 38 of the flexible sheet base 32 is unrolled or less tightly rolled than a remainder of the flexible implant 30. The unrolled or less-tightly rolled portion 66 at the end of the width 38 of the flexible sheet base 32 can include at least a portion of the tab 36. The unrolled or less-tightly rolled portion 66 can be adapted to extend out an elongate opening of a deployment device (e.g., the first elongate opening 27 of the deployment device 10 of FIG. 6).

Figure 12:
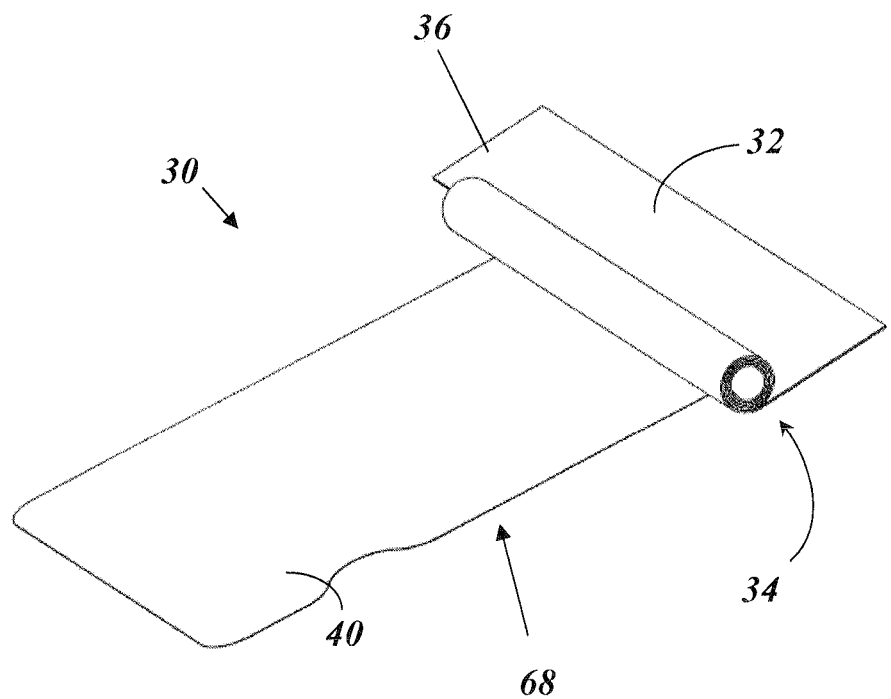
FIG. 12 is a perspective view of the flexible implant of FIG. 11B after being placed against a target site, unrolled, and subsequently released, according to aspects of the present invention.

The flexible sheet base 32 can be formed of a material that exhibits a tendency (e.g., a slight tendency) to remain in the rolled configuration after being unrolled. In such embodiments, the act of unrolling the flexible implant 30 and subsequently releasing the flexible implant 30 (e.g., letting go of the flexible implant 30) can cause a portion of the flexible sheet base 32 to re-furl and re-assume a rolled or partially rolled configuration. In illustrative embodiments, this re-furling or re-rolling of the flexible sheet base 32 is unmatched by the flexible separable layer 40 when the second major surface 68 of the flexible separable layer 40 is placed against (e.g., and applied to) a target site, such as an abdominal wall of a human. In illustrative embodiments, the flexible separable layer 40 (upon release of the flexible implant 30) remains adhered to the target site, e.g., in substantially the same shape and configuration as placed thereagainst. Accordingly, in such embodiments, the unmatched re-rolling of flexible sheet base 32 causes the flexible sheet base 32 to partially or completely separate from the flexible separable layer 40 during such re-rolling motion. Stated differently, the flexible implant 30 is adapted in such a way that the adhesive force between the target site (e.g., an abdominal wall of a human) and the flexible separable layer 40 is greater than the adhesive force between the flexible sheet base 32 and the flexible separable layer 40, such that the re-rolling of the flexible sheet base 32 after unrolling the flexible separable layer 40 onto the target site causes separation of the flexible sheet base 32 and the flexible separable layer 40. For example, FIG. 12 depicts the configuration of the flexible sheet base 32 and the flexible separable layer 40 relative to one another, as would be experienced during such re-rolling of the flexible sheet base 32 after applying the flexible separable layer 40 to a target site (e.g., an abdominal wall of a human). For clarity and purposes of illustration, the target site is not depicted in FIG. 12.

In some alternative embodiments, the flexible implant 30 is disposed in a double-rolled configuration rather than a single-rolled configuration. In such embodiments, the double-rolled configuration can be produced by rolling each end of the width 38 of the flexible sheet base 32 with the flexible separable layer 40 removably disposed thereon inward toward a center of the width 38, to produce two substantially parallel rolls of the flexible implant 30 (e.g., as substantially depicted herein and described previously with reference to FIGS. 3 and 4). The double-rolled configuration of the flexible implant 30 can be produced in such a way that the flexible separable layer 40 is disposed on an outward-facing surface of the two rolls, as would be appreciated by one of skill in the art upon reading the present specification.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A deployment system for a flexible separable layer, the deployment system comprising:
    an elongate housing with a chamber formed therein, the elongate housing having an elongate opening extending along a side thereof in such a way as to provide side access into the chamber; and
    a flexible implant disposed in the chamber of the housing, the flexible implant comprising a flexible sheet base and the flexible separable layer removably disposed on the flexible sheet base;
    wherein the flexible implant is removably disposed in the chamber of the housing in a rolled configuration in such a way that a portion of the flexible sheet base extends out through the elongate opening.

2. The deployment system of claim 1, wherein the flexible sheet base comprises a body portion and a tab extending from the body portion, the flexible separable layer being removably disposed on the body portion of the flexible sheet base.

3. The deployment system of claim 2, wherein the portion of the flexible sheet base that extends out through the elongate opening includes at least a portion of the tab.

4. The deployment system of claim 1, wherein the chamber has two closed ends.

5. The deployment system of claim 1, further comprising an end cap removably disposed on one of the two ends of the housing, wherein removal of the end cap opens one of the two ends of the chamber and provides access into the chamber.

6. The deployment system of claim 1, wherein the portion of the flexible sheet base extending out through the elongate opening extends beyond the housing in an amount capable of being gripped by a user.

7. The deployment system of claim 1, wherein the chamber has a closed end opposite the at least one open end and the housing comprises a portion extending beyond the closed end of the chamber adapted for being gripped by a positioning device.

8. The deployment system of claim 1, wherein the chamber is generally cylindrical in shape.

9. The deployment system of claim 1, wherein the flexible separable layer comprises a mesh.

10. The deployment system of claim 1, wherein the flexible separable layer comprises a film.

11. The deployment system of claim 1, wherein the flexible separable layer comprises a sheet-like prosthesis.

12. The deployment system of claim 1, wherein the housing is rigid.

13. The deployment system of claim 1, wherein the flexible sheet base and the flexible separable layer are adhered together.

14. The deployment system of claim 1, wherein the flexible sheet base and the flexible separable layer are adhered together by an adhesion tie layer, an adhesive coating, or both.

15. The deployment system of claim 1, wherein the flexible sheet base and the flexible separable layer are adhered together by one or more of heat, surface tension, or adhesion.

16. The deployment system of claim 1, wherein the flexible sheet base is adapted to independently assume a rolled configuration subsequent to unrolling the flexible implant in such a way that placing the flexible separable layer against a target site and releasing the flexible implant causes the flexible sheet base to separate from the flexible separable layer.

* * * * *